United States Patent
Fukushima et al.

(10) Patent No.: US 11,898,995 B2
(45) Date of Patent: Feb. 13, 2024

(54) METHOD FOR EVALUATING CRACK IN METAL MEMBER AND METHOD FOR EVALUATING FATIGUE DAMAGE IN METAL MEMBER

(71) Applicant: Mitsubishi Power, Ltd., Kanagawa (JP)

(72) Inventors: Hiroaki Fukushima, Tokyo (JP); Yuichi Hirakawa, Tokyo (JP); Hiroaki Yoshida, Yokohama (JP); Masahiko Yamashita, Yokohama (JP); Takeo Tokumoto, Yokohama (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 22 days.

(21) Appl. No.: 17/612,070

(22) PCT Filed: Jul. 2, 2020

(86) PCT No.: PCT/JP2020/025995
§ 371 (c)(1),
(2) Date: Nov. 17, 2021

(87) PCT Pub. No.: WO2021/002424
PCT Pub. Date: Jan. 7, 2021

(65) Prior Publication Data
US 2022/0349790 A1    Nov. 3, 2022

(30) Foreign Application Priority Data
Jul. 4, 2019 (JP) .................................. 2019-125456

(51) Int. Cl.
*G01N 3/06* (2006.01)
*G01N 33/2045* (2019.01)
*G01N 3/34* (2006.01)

(52) U.S. Cl.
CPC .............. *G01N 3/068* (2013.01); *G01N 3/34* (2013.01); *G01N 33/2045* (2019.01)

(58) Field of Classification Search
CPC ...... G01N 3/068; G01N 3/34; G01N 33/2045; G01N 3/60; G01N 2203/0062; G01N 3/32;
(Continued)

(56) References Cited

U.S. PATENT DOCUMENTS
4,711,707 A    12/1987    Kikuchi et al.

FOREIGN PATENT DOCUMENTS
CN    102719688 B  *  9/2013
CN    107525061       12/2017
(Continued)

OTHER PUBLICATIONS

International Search Report dated Sep. 1, 2020 in corresponding International Application No. PCT/JP2020/025995, with English translation.
(Continued)

*Primary Examiner* — Marrit Eyassu
(74) *Attorney, Agent, or Firm* — Wenderoth, Lind & Ponack, L.L.P.

(57) ABSTRACT

A method for evaluating a crack in a metal member comprises a first removal step (S10) and a second removal step (S20). In the first removal step (S10), a step for electrolyzing a metal member having an oxide scale formed on a surface thereof, a step for acquiring an image of the oxide scale as a first image, and a step for determining whether or not a scale crack has occurred are repeated until occurrence of a scale crack is determined. In the second removal step (S20), a step for electrolyzing the metal member having the scale crack, a second image acquisition step for acquiring an image of the oxide scale as a second image, and a second
(Continued)

determination step for determining whether or not the scale crack has disappeared are repeated until disappearance of the oxide scale is determined.

9 Claims, 8 Drawing Sheets

(58) Field of Classification Search
CPC .............. G01N 3/02; G01N 2203/0005; G01N 2203/0073; G01N 1/32
USPC .......................................................... 73/800
See application file for complete search history.

(56) References Cited

FOREIGN PATENT DOCUMENTS

| JP | 53-116231 | 10/1978 |
|---|---|---|
| JP | 06-285720 | 10/1994 |
| JP | 7-128327 | 5/1995 |
| JP | 10-160646 | 6/1998 |
| JP | 2862449 | 3/1999 |
| JP | 2008-051659 | 3/2008 |
| JP | 2009-175110 | 8/2009 |
| JP | 2009175110 A * | 8/2009 |
| JP | 2013-139744 | 7/2013 |
| JP | 2013134022 A * | 7/2013 |
| JP | 2013139744 A * | 7/2013 |
| JP | 2014-224720 | 12/2014 |
| JP | 6276963 | 2/2018 |

OTHER PUBLICATIONS

Written Opinion of the International Searching Authority dated Sep. 1, 2020 in corresponding International Application No. PCT/JP2020/025995, with English translation.

* cited by examiner

METHOD FOR EVALUATING CRACK IN METAL MEMBER AND METHOD FOR EVALUATING FATIGUE DAMAGE IN METAL MEMBER

TECHNICAL FIELD

The present invention relates to a method for evaluating a crack in a metal and a method for evaluating fatigue damage in a metal.

Priority is claimed on Japanese Patent Application No. 2019-125456, filed Jul. 4, 2019, the content of which is incorporated herein by reference.

BACKGROUND ART

In a high-temperature device, such as a steam turbine, micro surface cracks may be generated on a metal due to fatigue damage caused by thermal stress. For this reason, it is desirable to observe surface cracks and perform maintenance at an appropriate timing during the confirmation of the high-temperature device.

For example, PTL 1 discloses a technique that observes microcracks of an object to be measured subjected to a fatigue test and calculates the fatigue damage rate of a structure on the basis of the sum of the lengths of two or more microcracks, which include a microcrack having the maximum length among the observed microcracks, and a fatigue damage rate based on the object to be measured.

CITATION LIST

Patent Literature

[PTL 1] Japanese Unexamined Patent Application Publication No. 2014-224720

SUMMARY OF INVENTION

Technical Problem

Incidentally, oxide scale may be generated on the surface of a metal at a portion where temperature is high, particularly, a portion exposed to the steam of a steam turbine or the like. In such a case, it is necessary to remove scale prior to observing the surface cracks of the metal as in PTL 1. However, in a case where the removal of scale is not performed appropriately in the descaling process, there is a possibility that not only scale but also surface cracks generated on the surface of the metal will be removed due to the excessive removal of scale. For this reason, there is a case where the damage of the metal cannot be appropriately evaluated through the observation of surface cracks depending on the proficiency level or skill of a worker.

The present invention has been made in consideration of the above-mentioned circumstances, and an object of the present invention is to provide a method for evaluating a crack in a metal and a method for evaluating fatigue damage in a metal that can correctly evaluate the cracks of a metal without requiring proficiency.

Solution to Problem

The present invention employs the following means in order to achieve the object.

According to a first aspect of the present invention, a method for evaluating a crack in a metal includes a first removal step, a second removal step, and an evaluation step. In the first removal step, electrolytic treatment is performed on a metal having an oxide scale layer formed on a surface thereof until a scale crack is generated in the oxide scale layer. In the second removal step, the electrolytic treatment is performed until the scale crack generated in the first removal step disappears, that is, the oxide scale layer is removed. In the evaluation step, a crack on a surface of a base material of the metal from which the oxide scale layer has been completely removed in the second removal step is measured and evaluated.

In this way, a scale crack can be generated on the surface of the oxide scale layer by the first removal step. Then, in the second removal step, the electrolytic treatment is allowed to proceed on the basis of the state of the scale crack and can be completed when the scale crack disappears. For this reason, it is possible to suppress that a crack generated on the surface of the base material of the metal cannot be measured correctly since the oxide scale layer remains, or corrosion occurs on the surface of the base material since the electrolytic treatment continues to be performed even after the oxide scale layer has been removed. Accordingly, it is possible to correctly evaluate the crack of the metal without requiring proficiency.

According to a second aspect of the present invention, the first removal step according to the first aspect may include a step of performing the electrolytic treatment on the metal having oxide scale generated on the surface thereof, a step of acquiring a first image by imaging the oxide scale, and a step of determining whether or not the scale crack has been generated in the oxide scale on the basis of the first image. The second removal step according to the first aspect may include a step of performing the electrolytic treatment on the metal in which the scale crack is generated, a step of acquiring a second image by imaging the oxide scale, and a step of determining whether or not the scale crack has disappeared on the basis of the second image.

In this way, the electrolytic treatment is performed on the oxide scale generated on the surface of the metal, it is confirmed that a scale crack is generated in the oxide scale, and the electrolytic treatment is then performed repeatedly until the generated scale crack disappears. Accordingly, it is possible to suppress that the scale crack generated in the oxide scale is mistaken for a surface crack generated in the metal, and the electrolytic treatment ends before the oxide scale is removed. Therefore, since the disappearance of the scale crack means that the oxide scale has been removed, it is possible to cause the surface of the base material of the metal in which the surface crack is generated to be easily exposed.

According to a third aspect of the present invention, in the first removal step according to the second aspect, a first master image, which is obtained in a state where the scale crack is generated on a surface of the oxide scale, and the first image may be compared with each other in a case where it is to be determined whether or not the scale crack has been generated on the surface of the oxide scale.

Since the first image is compared with the first master image as described above, it is possible to more easily and accurately ascertain that the scale crack is generated on the surface of the oxide scale.

According to a fourth aspect of the present invention, in the second removal step according to the second or third aspect, a second master image, which is obtained in a state where the scale crack has disappeared, and the second image may be compared with each other in a case where it is to be determined whether or not the scale crack has disappeared.

Since the second image is compared with the second master image as described above, it is possible to more easily and accurately ascertain that the scale crack has disappeared.

According to a fifth aspect of the present invention, the second removal step according to any one aspect of the second to fourth aspects may further include a step of setting a time for which the electrolytic treatment is to be performed on the metal in which the scale crack is generated in a case where it is determined that the scale crack has not disappeared.

In this way, it is possible to suppress that corrosion caused by a chemical solution occurs on the metal due to excessive electrolytic treatment.

According to a sixth aspect of the present invention, in the method for evaluating a crack in a metal according to the fifth aspect, master data in which a state of the scale crack is associated with an electrolytic treatment time that is required for the scale crack to disappear, which is set according to the state of the scale crack, may be prepared in advance. In the step of setting a time for which the electrolytic treatment is to be performed, the time for which the electrolytic treatment is to be performed on the metal in which the scale crack is generated may be set on the basis of the second image and the master data.

Since a time for which the electrolytic treatment is to be performed is set on the basis of the second image and the master data as described above, it is easy to appropriately set a time for which the electrolytic treatment is to be performed without requiring proficiency.

According to a seventh aspect of the present invention, in the step of setting a time for which the electrolytic treatment is to be performed according to the fifth or sixth aspect the time for which the electrolytic treatment is to be performed on the metal in which the scale crack is generated may be set on the basis of a growth direction of the scale crack.

In this way, it is easy to appropriately set a time for which the electrolytic treatment is to be performed.

According to an eighth aspect of the present invention, in the step of setting a time for which the electrolytic treatment is to be performed according to any one aspect of the fifth to seventh aspects, the time for which the electrolytic treatment is to be performed on the metal in which the scale crack is generated may be set on the basis of a width dimension of the scale crack.

According to this configuration, it is easy to appropriately set a time for which the electrolytic treatment is to be performed.

According to a ninth aspect of the present invention, the electrolytic treatment according to any one aspect of the first to eighth aspects may be performed in a strongly acid solution that does not contain a corrosion inhibitor for inhibiting corrosion of the metal.

In this way, the electrolytic treatment ends in a case where the scale crack disappears, the oxide scale is removed, and the surface of the metal is exposed. Accordingly, even though a corrosion inhibitor is not used, treatment for removing the oxide scale can be appropriately performed in a strongly acid solution.

According to a tenth aspect of the present invention, a method for evaluating fatigue damage in a metal includes evaluating a degree of fatigue damage of the metal on a basis of a state of a crack formed on the surface of the base material of the metal that is evaluated by the method for evaluating a crack in a metal according to any one aspect of the first to ninth aspects.

Advantageous Effects of Invention

According to the method for evaluating a crack in a metal and the method for evaluating fatigue damage in a metal, it is possible to correctly evaluate the crack of a metal without requiring proficiency.

DESCRIPTION OF EMBODIMENTS

A method for evaluating a crack in a metal and a method for evaluating fatigue damage in a metal according to an embodiment of the present invention will be described below with reference to the drawings.

Figure 1:
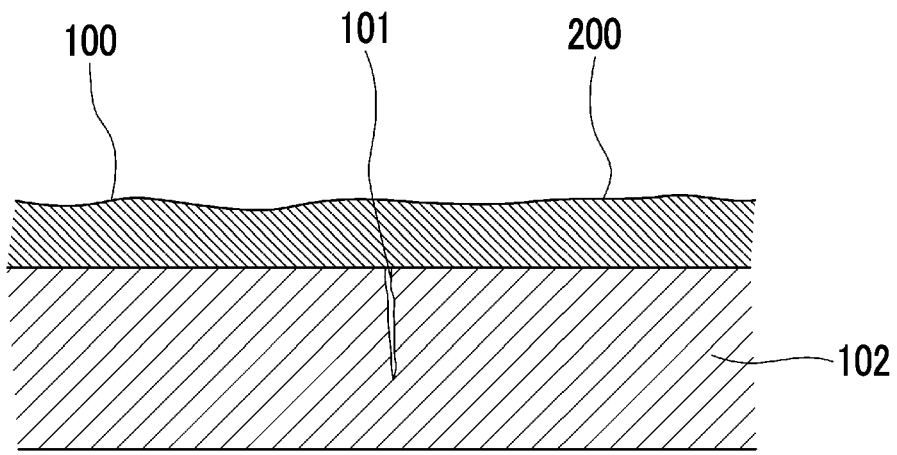
FIG. 1 is a cross-sectional view showing an example of a metal that is an object to be evaluated by a method for evaluating a crack in a metal and a method for evaluating fatigue damage in a metal according to an embodiment.

FIG. 1 is a cross-sectional view showing an example of a metal that is an object to be evaluated by the method for evaluating a crack in a metal and the method for evaluating fatigue damage in a metal according to this embodiment.

The state of generation of micro surface cracks 101 generated on the surface of a metal 100 as shown in FIG. 1 is evaluated in the method for evaluating a crack in a metal according to this embodiment. Further, for example, the remaining life and the like of the metal 100 are predicted on the basis of evaluation results obtained from the evaluation of the state of generation of the surface cracks 101. In this embodiment, the use of the evaluation results of the state of generation of the surface cracks 101 is not limited in any way, and the evaluation results of the state of generation of the surface cracks 101 may be used for uses other than the prediction of the remaining life of the metal 100 based on the evaluation results. Furthermore, methods for predicting the remaining life and the like of the metal 100 based on the evaluation results are also not limited in any way.

The metal 100 of this embodiment is provided in, for example, a high-temperature device (not shown), which includes a flow passage portion for high-temperature fluid of a steam turbine or the like. Since the metal 100 is provided in the flow passage portion in which high-temperature fluid flows and is exposed to the high-temperature fluid during the operation of the high-temperature device, thermal stress acts on the metal 100. Micro surface cracks 101 may be generated on the surface of this metal 100 due to thermal fatigue where thermal stress repeatedly acts. Further, since the metal 100 is exposed to the high-temperature fluid, an oxide scale layer 200 is formed on the surface of a base material 102 over time. Since the high-temperature fluid is in contact with the surface of the base material 102 of the metal 100, the base material of the metal 100 is oxidized, and the oxide scale layer 200 is generated.

In the method for evaluating a crack in a metal according to this embodiment, the state of the surface cracks 101 of the metal 100 is evaluated after the oxide scale layer 200 generated on the surface of the base material 102 of the metal 100 is removed so that the surface of the metal 100 is exposed to the outside. With regard to the metal 100 that is an object to be evaluated by this method for evaluating a crack, for example, the shape of the metal 100 to be exposed to high temperature is discontinuous and the metal 100 is provided at a portion where the concentration of stress is likely to occur. A stress analysis method using, for example, finite element method (FEM) analysis or the like can be used to select a portion where the concentration of stress is likely to occur as described above. In a case where FEM analysis is performed on the basis of data, which are measured by an actual device, such as the operating temperature and temperature change state of the high-temperature device (not shown), a portion where the concentration of stress is likely to occur and a degree of damage is likely to increase can be selected.

Figure 2:
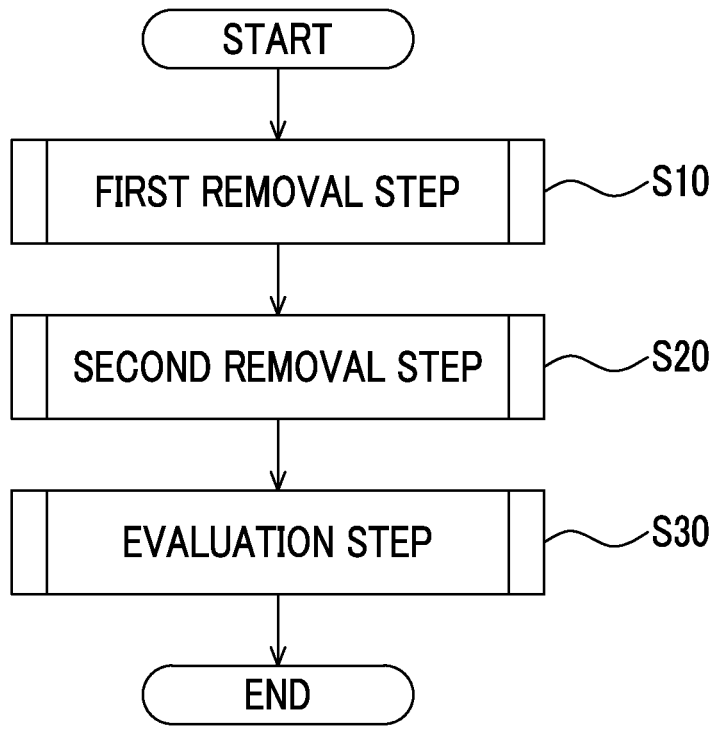
FIG. 2 is a flowchart showing the flow of the method for evaluating a crack in a metal according to this embodiment.

FIG. 2 is a flowchart showing the flow of the method for evaluating a crack in a metal according to this embodiment.

As shown in FIG. 2, the method for evaluating a crack in a metal includes a first removal step S10, a second removal step S20, and an evaluation step S30. In the first removal step S10, the oxide scale layer 200 generated on the surface of the base material 102 of the metal 100 is removed until scale cracks 201 (see FIG. 9) generated in the oxide scale layer 200 are exposed. In the second removal step S20, the oxide scale layer 200 in which the scale cracks 201 are generated in the first removal step S10 is further removed so that the surface of the metal 100 is exposed. In the evaluation step S30, the state of the surface cracks 101 exposed to the surface of the metal 100 is evaluated.

(First Removal Step S10)

Figure 3:
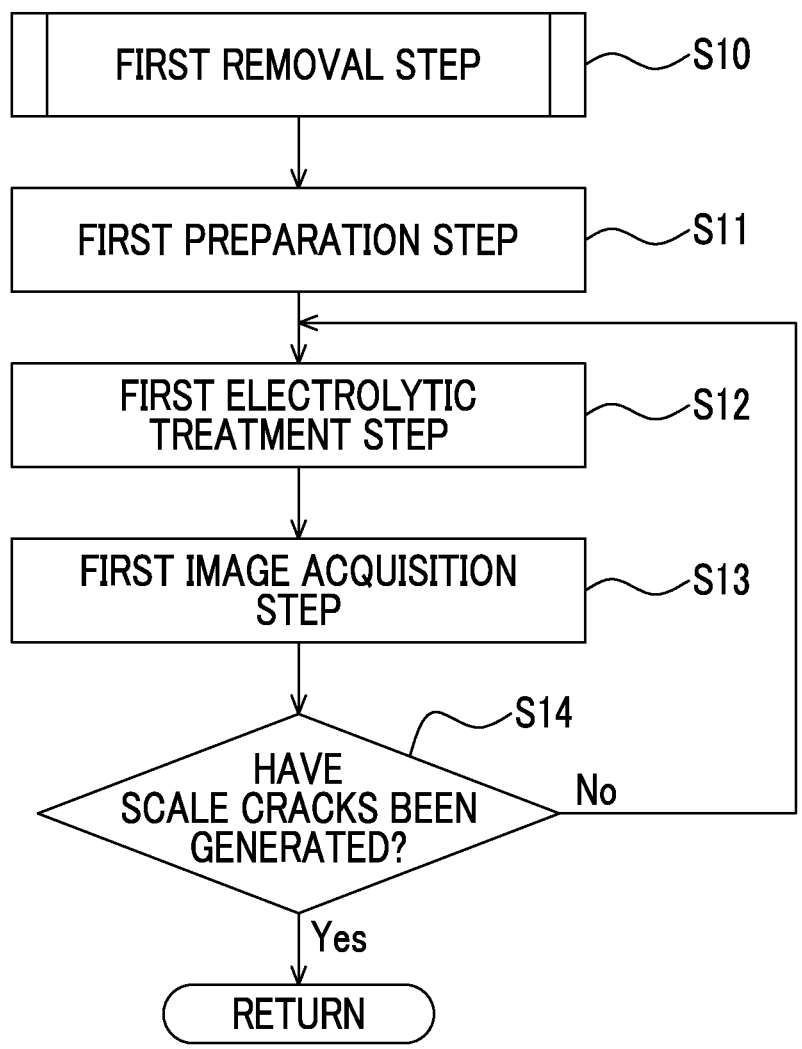
FIG. 3 is a flowchart showing the detailed flow of a first removal step of the method for evaluating a crack in a metal according to this embodiment.
Figure 4:
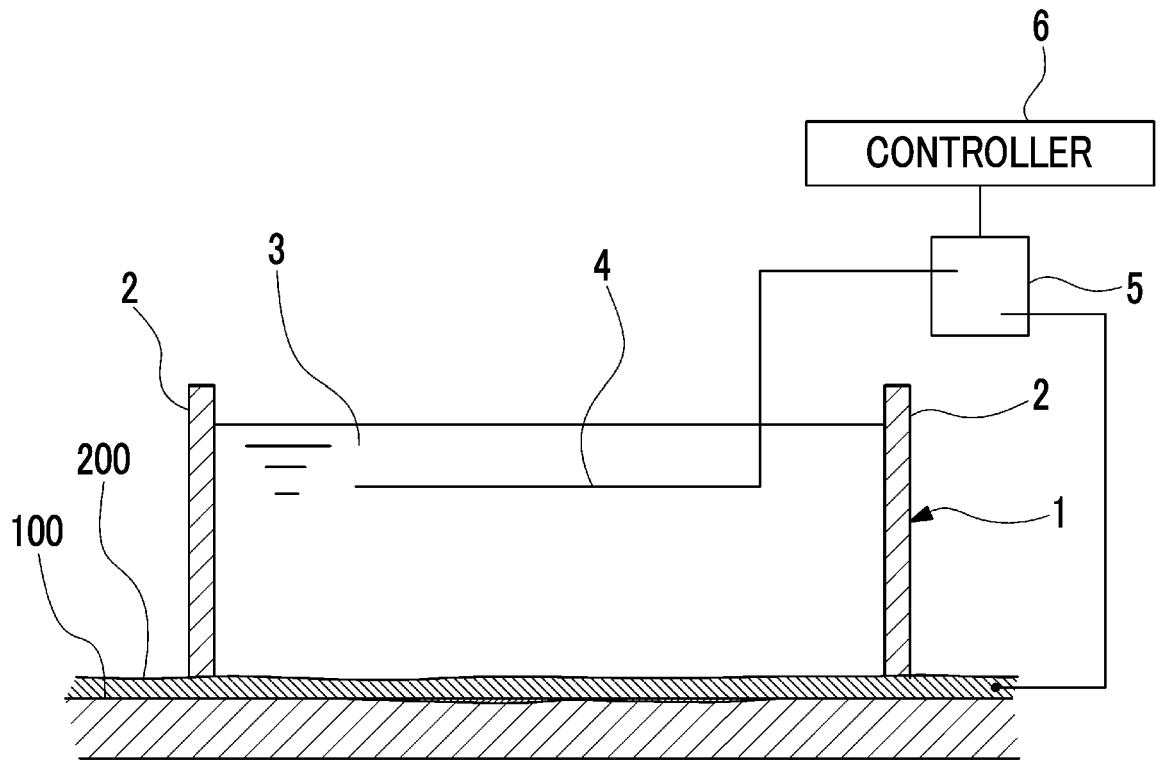
FIG. 4 is a diagram showing an example of an electrolytic cell that is used to remove oxide scale in the method for evaluating a crack in a metal according to this embodiment.

FIG. 3 is a flowchart showing the detailed flow of the first removal step of the method for evaluating a crack in a metal according to this embodiment. FIG. 4 is a diagram showing an example of an electrolytic cell that is used to remove oxide scale in the method for evaluating a crack in a metal according to this embodiment.

As shown in FIG. 3, the first removal step S10 includes a first preparation step S11, a first electrolytic treatment step S12, a first image acquisition step S13, and a first determination step S14.

For example, as shown in FIG. 4, an electrolytic cell 1 for storing an electrolytic solution 3 is prepared in the first preparation step S11. For example, a partition wall 2 rising upward from the surface of the metal 100 is provided so as to surround a portion to be evaluated of the metal 100, so that the electrolytic cell is formed. Further, the electrolytic cell 1 may be separately provided outside the high-temperature device in a case where the metal 100 can be detached from the high-temperature device. In this case, a bottomed electrolytic cell opened upward may be used as the electrolytic cell 1.

The electrolytic solution 3 is stored in the electrolytic cell 1. A strongly acid solution, for example, a sulfuric acid aqueous solution can be used as the electrolytic solution 3. Here, an electrolytic solution, which does not contain a corrosion inhibitor (referred to as an inhibitor) for inhibiting the corrosion of the metal 100, is used as the electrolytic solution 3 exemplified in this embodiment. In a case where this corrosion inhibitor is contained in the electrolytic solution 3, the dissolution and corrosion of the base material 102 itself of the metal 100 can be inhibited. However, since it may be difficult to obtain the corrosion inhibitor, in order to cope with such circumstances, the corrosion inhibitor is not contained in the electrolytic solution 3 in this embodiment.

In the first preparation step S11, an electrode 4 made of, for example, platinum is further disposed in the electrolytic solution 3 so as to face the surface of the metal 100. In addition, a power supply 5 is provided between the electrode 4 and the metal 100.

In the first electrolytic treatment step S12, electrolytic treatment is performed on the metal 100 where the oxide scale layer 200 is generated on the surface of the base material 102. For this purpose, a voltage is applied between the electrode 4 and the oxide scale layer 200 of the metal 100 by the power supply 5. In the electrolytic cell 1, a predetermined voltage continues to be applied between the electrode 4 and the oxide scale layer 200 of the metal 100 by the power supply 5 for a set time that is set in a controller 6.

In a case where the electrode 4 is used as an anode and the metal 100 is used as a cathode during the electrolytic treatment, electrons are moved to the power supply 5 from the metal 100 that is used as acathode which is in contact with the electrolytic solution 3 through the oxide scale layer 200. Accordingly, hydrogen gas is generated on the surface of the metal 100 disposed immediately below the oxide scale layer 200. The oxide scale layer 200 is broken by the pressure of the generated hydrogen gas (bubbles), so that scale cracks are generated, and the oxide scale layer 200 is separated after that.

In the first electrolytic treatment step S12, a set time for which the electrolytic treatment is to be performed on the metal 100 can be set to a predetermined value (for example, 30 minutes or the like). Further, a worker can also arbitrarily set a time for which the electrolytic treatment is to be performed. A time for which the electrolytic treatment is to be performed in the first electrolytic treatment step S12 is set in the controller 6 of the electrolytic cell 1.

Figure 5:
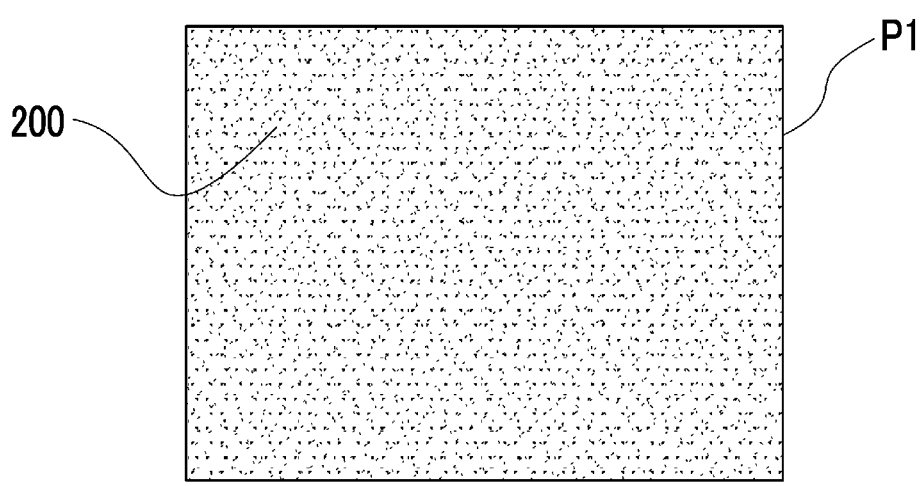
FIG. 5 is a perspective view showing an example of an image that is acquired in a first image acquisition step according to this embodiment.
Figure 6:
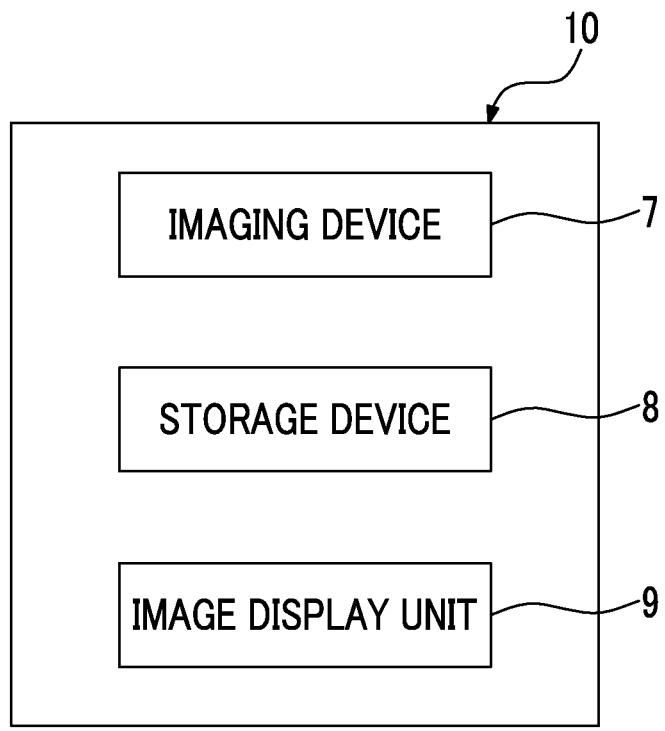
FIG. 6 is a functional block diagram of an observation apparatus that is used in the method for evaluating a crack in a metal according to this embodiment.
Figure 7:
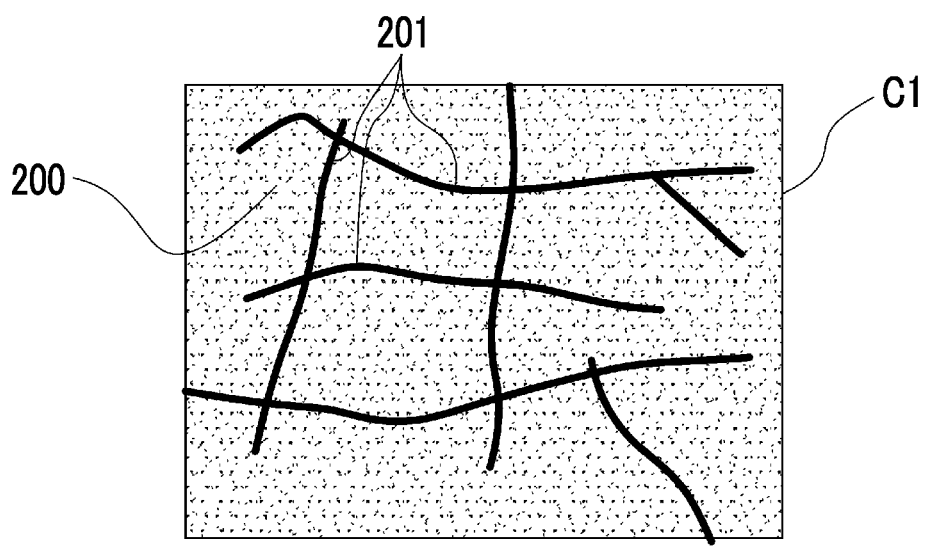
FIG. 7 is a diagram showing an example of a first master image that is used in the method for evaluating a crack in a metal according to this embodiment.

FIG. 5 is a diagram showing an example of an image that is acquired in the first image acquisition step according to this embodiment. FIG. 6 is a functional block diagram of an observation apparatus that is used in the method for evaluating a crack in a metal according to this embodiment. FIG. 7 is a diagram showing an example of a first master image that is used in the method for evaluating a crack in a metal according to this embodiment.

In the first image acquisition step S13, after the electrolytic treatment is performed for a predetermined time in the first electrolytic treatment step S12, the surface of the oxide scale layer 200 is imaged and, for example, a first image P1 shown in FIG. 5 is acquired. For this purpose, a method that includes using replica film (acetyl cellulose film) and magnifying the transferred surface state of the oxide scale layer 200 with a microscope or the like to acquire the first image P1 can be applied. Further, a method such as directly magnifying the oxide scale layer 200 with a microscope or the like to acquire the first image P1 can also be applied. A magnified image captured by the microscope or the like is taken by an imaging device 7, such as a digital camera, provided in an observation apparatus 10 shown in FIG. 6, so that the first image P1 can be acquired.

In a case where the surface of the oxide scale layer 200 cannot be observed or imaged in a state where the metal 100 is immersed in the electrolytic solution 3, the surface of the oxide scale layer 200 is observed or imaged after the electrolytic solution 3 stored in the electrolytic cell 1 is removed.

In the first determination step S14, whether or not the scale cracks 201 have been generated in the oxide scale layer 200 is determined on the basis of the first image P1. In the first determination step S14, a first master image C1 obtained in a state where the scale cracks 201 are generated on the surface of the oxide scale layer 200 as shown in FIG. 7 is prepared in advance. The first master image C1 prepared in advance is stored in a storage device 8 of the observation apparatus 10 shown in FIG. 6 in advance. In the first determination step S14, the first master image C1 stored in advance is called from the storage device 8 and is displayed on an image display unit 9, such as a monitor. A worker compares the first master image C1 displayed on the image display unit 9 with the first image P1 to determine whether or not the scale cracks 201 have been generated on the surface of the oxide scale layer 200. The comparison of the first image P1 and the first master image C1 may be performed through the image processing of an image processing device (not shown).

Here, the growth directions of the scale cracks 201 formed in the oxide scale layer 200 are random. In contrast, the surface cracks 101 formed in the base material itself of the metal 100 are affected by stress acting on the metal 100. Specifically, since a plurality of surface cracks 101 extend according to directions in which stress acts, the growth directions of the surface cracks 101 are aligned. Accordingly, in a case where the growth directions of visible cracks are random, it is possible to easily specify in the first determination step S14 that the cracks are the scale cracks 201.

As a result of comparison of the first master image C1 and the first image P1, in a case where it is determined in the first image P1 acquired in the first image acquisition step S13 that the scale cracks 201 are generated on the surface of the oxide scale layer 200 ("Yes" in Step S14), the process returns to the main flow shown in FIG. 2 and proceeds to the second removal step S20.

As a result of comparison of the first master image C1 and the first image P1, in a case where it is determined in the first image P1 acquired in the first image acquisition step S13 that the scale cracks 201 are not generated on the surface of the oxide scale layer 200 ("No" in Step S14), an electrolytic solution 3 is put in the electrolytic cell 1, and the first electrolytic treatment step S12 is repeated.

In this way, the first electrolytic treatment step S12, the first image acquisition step S13, and the first determination step S14 are repeated in the first removal step S10 until it is determined in the first determination step S14 that the scale cracks 201 have been generated.

(Second Removal Step S20)

Figure 8:
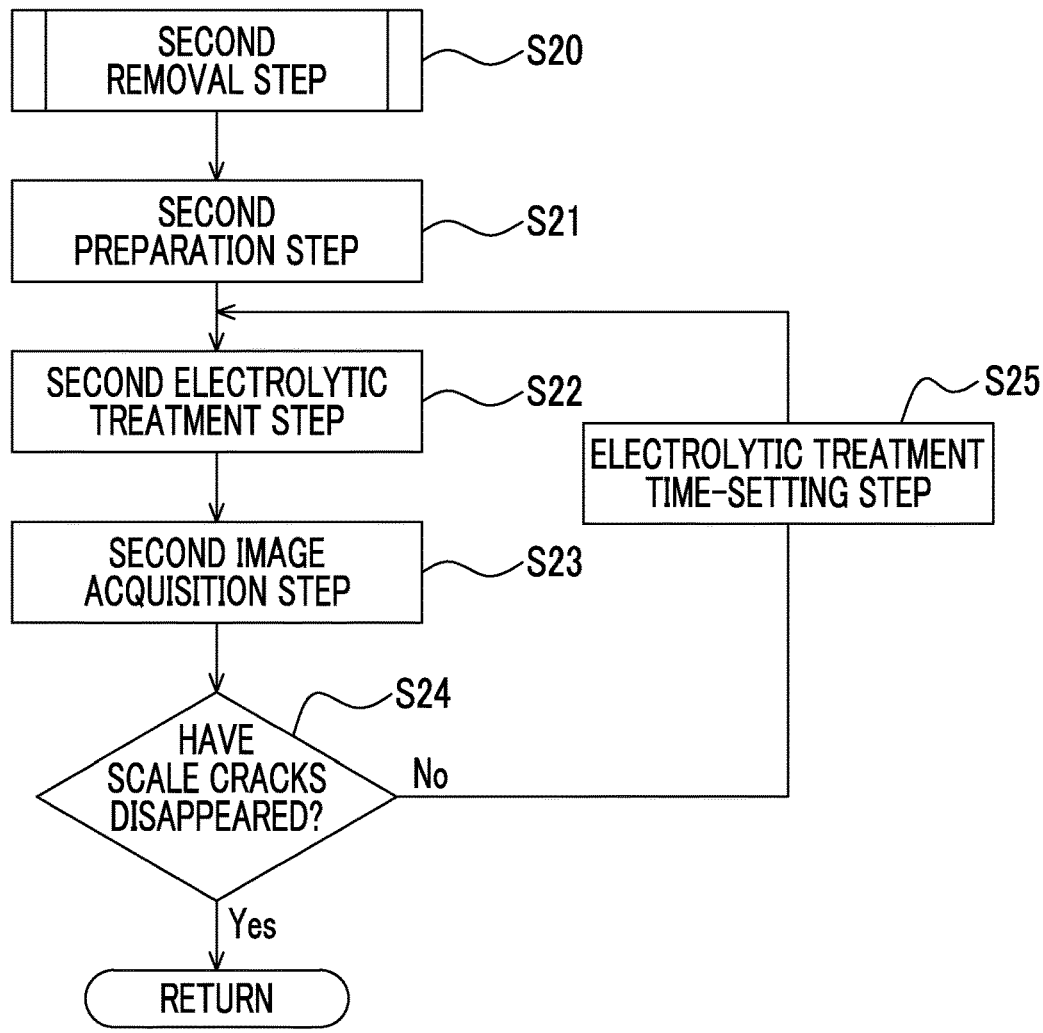
FIG. 8 is a flowchart showing the detailed flow of a second removal step of the method for evaluating a crack in a metal according to this embodiment.

FIG. 8 is a flowchart showing the detailed flow of the second removal step of the method for evaluating a crack in a metal according to this embodiment.

As shown in FIG. 8, the second removal step S20 includes a second preparation step S21, a second electrolytic treatment step S22, a second image acquisition step S23, a second determination step S24, and an electrolytic treatment time-setting step S25.

In the second preparation step S21, an electrolytic solution 3 is stored in the electrolytic cell 1 as in the first preparation step S11. Further, the electrode 4 made of, for example, platinum is disposed in the electrolytic solution 3 so as to face the surface of the metal 100. In addition, a power supply 5 is provided between the electrode 4 and the metal 100.

In the second electrolytic treatment step S22, electrolytic treatment is performed on the metal 100 including an oxide scale layer 200 which includes the scale cracks 201 generated on the surface thereof since being subjected to the first removal step S10. In the second electrolytic treatment step S22, a time (treatment time) for which the electrolytic treatment is to be performed on the metal 100 having the scale cracks 201 generated on the surface thereof can be set to a preset value (for example, 5 minutes, 30 minutes, or the like). Further, a worker can also arbitrarily set a time for which the electrolytic treatment is to be performed. A time for which the electrolytic treatment is to be performed in the second electrolytic treatment step S22 is set in the controller 6 of the electrolytic cell 1.

Figure 9:
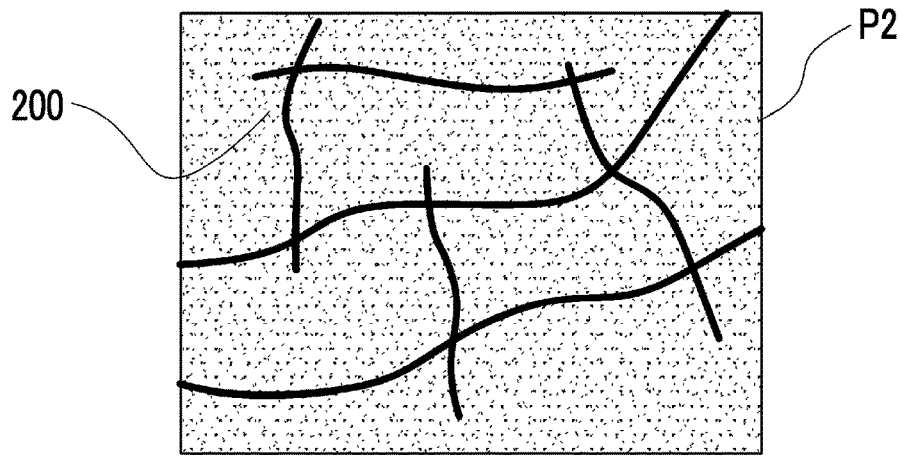
FIG. 9 is a diagram showing an example of an image that is acquired in a second image acquisition step according to this embodiment.

FIG. 9 is a diagram showing an example of an image that is acquired in the second image acquisition step according to this embodiment.

In the second image acquisition step S23, after the electrolytic treatment is performed for a predetermined time in the second electrolytic treatment step S22, the surface of the oxide scale layer 200 is imaged and, for example, a second image P2 shown in FIG. 9 is acquired. Even in this case, a method that includes using replica film (acetyl cellulose film) and magnifying the transferred surface state of the oxide scale layer 200 with a microscope or the like to acquire the second image P2 can be applied. Further, a method such as directly magnifying the oxide scale layer 200 with a microscope or the like to acquire the second image P2 can also be applied. A magnified image captured by the microscope or the like is taken by the imaging device 7, such as a digital camera, so that the second image P2 can be acquired. Even at this time, in a case where the surface of the oxide scale layer 200 cannot be observed or imaged in a state where the metal 100 is immersed in the electrolytic solution 3, the surface of the oxide scale layer 200 is observed or imaged after the electrolytic solution 3 stored in the electrolytic cell 1 is removed.

Figure 10:
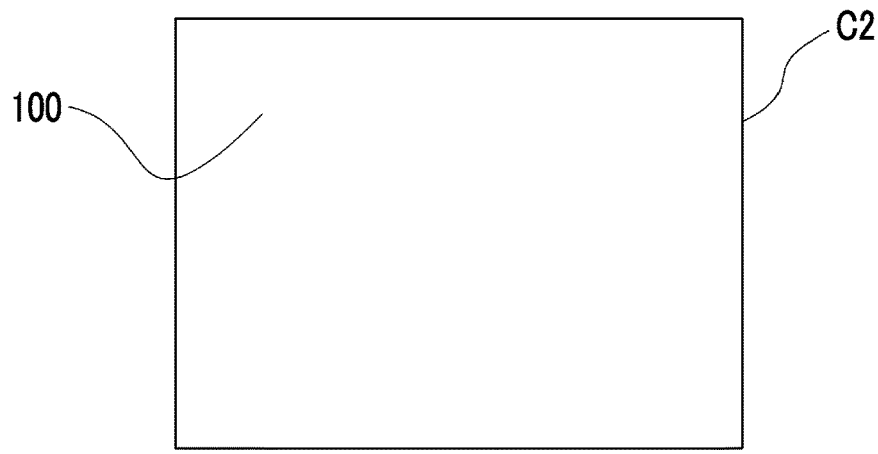
FIG. 10 is a diagram showing an example of a second master image that is used in a second determination step according to this embodiment.

FIG. 10 is a diagram showing an example of a second master image that is used in the second determination step according to this embodiment.

In the second determination step S24, whether or not the scale cracks 201 have disappeared is determined on the basis of the second image P2. In the second determination step S24, for example, a second master image C2 shown in FIG. 10 obtained in a state where the scale cracks 201 disappear is prepared in advance. The disappearance of the scale cracks 201 means that the oxide scale layer 200 itself, in which the scale cracks 201 are generated, is also removed, and the surface of the metal 100 is exposed. That is, the second master image C2 is the image of the surface of the base material 102 of the metal 100 from which the scale cracks 201 and the oxide scale layer 200 have disappeared. This second master image C2 is stored in the storage device 8 in advance. In the second determination step S24, the second master image C2 stored in advance is called from the storage device 8 and is displayed on the image display unit 9, such as a monitor. A worker compares the second master image C2, which is displayed on the image display unit 9, with the second image P2, which is acquired in the second image acquisition step S23, to determine whether or not the scale cracks 201 have disappeared. The comparison of the second image P2 and the second master image C2 may be performed through the image processing of the image processing device (not shown).

As a result of comparison of the second master image C2 and the second image P2, in a case where it is determined in the second image P2 acquired in the second image acquisition step S23 that the scale cracks 201 have disappeared ("Yes" in Step S24), the process returns to the main flow shown in FIG. 2 and proceeds to the evaluation step S30.

As a result of comparison of the second master image C2 and the second image P2, in a case where it is determined in the second image P2 acquired in the second image acquisition step S23 that the scale cracks 201 have not disappeared ("No" in Step S24), the process proceeds to the electrolytic treatment time-setting step S25.

In a case where it is determined that the scale cracks 201 have not disappeared, in other words, the scale cracks 201 have appeared, a time for which the electrolytic treatment is to be performed on the metal 100 in which the scale cracks 201 are generated is set in the electrolytic treatment time-setting step S25. For this purpose, a plurality of types of reference images (master data) M with the degrees of progress of the removal of the oxide scale layer 200 different from each other are prepared in advance. For example, the width dimensions of exposed scale cracks 201 are different from each other in a plurality of types of reference images M1 to M3. As the degrees of disappearance of the scale cracks 201 progress, the width dimensions of the scale cracks 201 gradually increase. Accordingly, as the width dimensions become greater, a time for which the electrolytic treatment is to be performed until the exposed scale cracks 201 completely disappear (hereinafter referred to as an electrolytic treatment time) becomes shorter.

Electrolytic treatment times T that are required for the scale cracks 201 with width dimensions in the reference images M to completely disappear are associated with the plurality of types of reference images M (M1 to M3) on the basis of experiments and the like performed in advance. Data of the plurality of types of reference images M and the electrolytic treatment times T, which are associated with each other in this way, are stored in the storage device 8 in advance.

Figure 11:
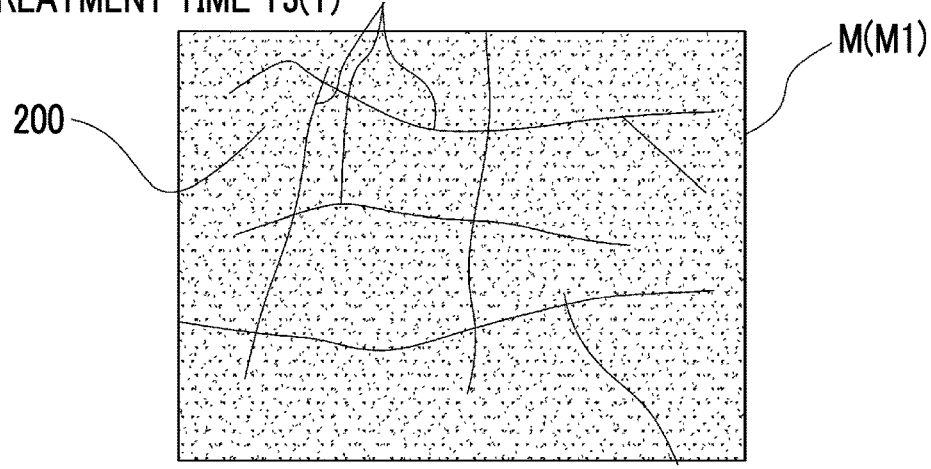
FIG. 11 is a diagram showing an example of a reference image that is used in an electrolytic treatment time-setting step according to this embodiment.
Figure 12:
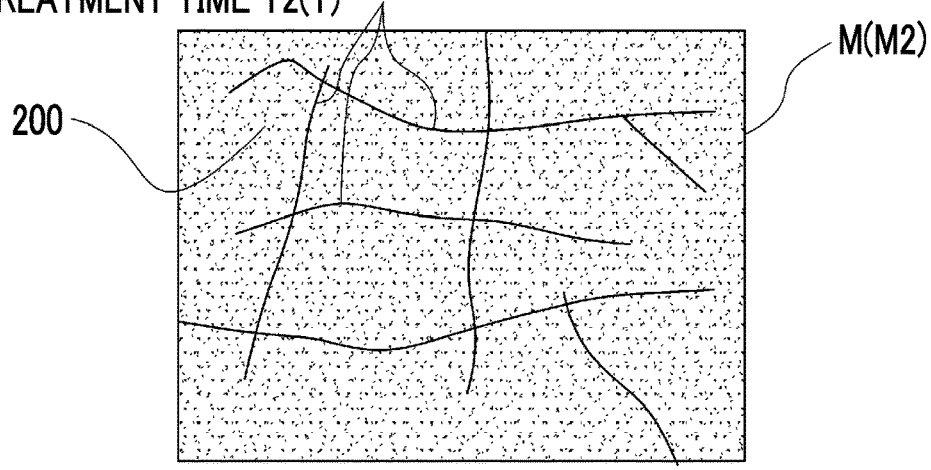
FIG. 12 is a diagram showing another example of the reference image that is used in the electrolytic treatment time-setting step according to this embodiment.
Figure 13:
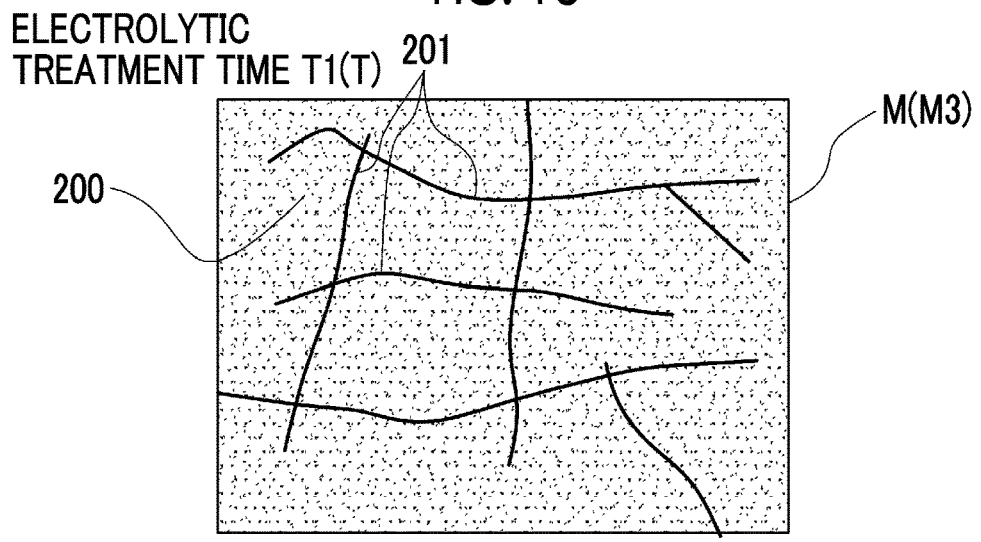
FIG. 13 is a diagram showing still another example of the reference image that is used in the electrolytic treatment time-setting step according to this embodiment.

FIGS. 11 to 13 are diagrams showing examples of the reference image that is used in the electrolytic treatment time-setting step according to this embodiment.

In the electrolytic treatment time-setting step S25, for example, the plurality of types of reference images M (M1 to M3) shown in FIGS. 11 to 13 are called from the storage device 8 and are displayed on the image display unit 9, such as a monitor, together with the second image P2 acquired in the second image acquisition step S23. A worker compares the plurality of types of reference images M (M1 to M3), which are displayed on the image display unit 9, with the second image P2. The worker selects an image, which is closest to the state (for example, width dimensions or the like) of the scale cracks 201 of the second image P2, from the plurality of types of reference images M (M1 to M3). Then, since electrolytic treatment times T1 to T3 associated with the selected reference image M are specified, the worker sets the specified electrolytic treatment time T in the controller 6 of the electrolytic cell 1. An electrolytic treatment time to be actually set in the controller 6 may not be the specified electrolytic treatment time T. For example, the worker may appropriately set an electrolytic treatment time on the basis of the specified electrolytic treatment time T.

After the setting of the electrolytic treatment time T is completed in the electrolytic treatment time-setting step S25, the process returns to the second preparation step S21 and the immersion of the metal 100 in the electrolytic solution 3 stored in the electrolytic cell 1 and the electrolytic treatment of the metal 100 performed in the second electrolytic treatment step S22 are repeated. In the second electrolytic treatment step S22, the electrolytic treatment of the metal 100 performed in the electrolytic solution 3 is repeated according to the electrolytic treatment time T set in the electrolytic treatment time-setting step S25.

In this way, the second electrolytic treatment step S22, the second image acquisition step S23, the second determination step S24, and the electrolytic treatment time-setting step S25 are repeated in the second removal step S20 until it is determined in the second determination step S24 that the scale cracks 201 have disappeared.

In a case where it is determined in the second determination step S24 that the scale cracks 201 have disappeared, the process returns to the main flow shown in FIG. 2 and proceeds to the evaluation step S30.

(Evaluation Step S30)

Figure 14:
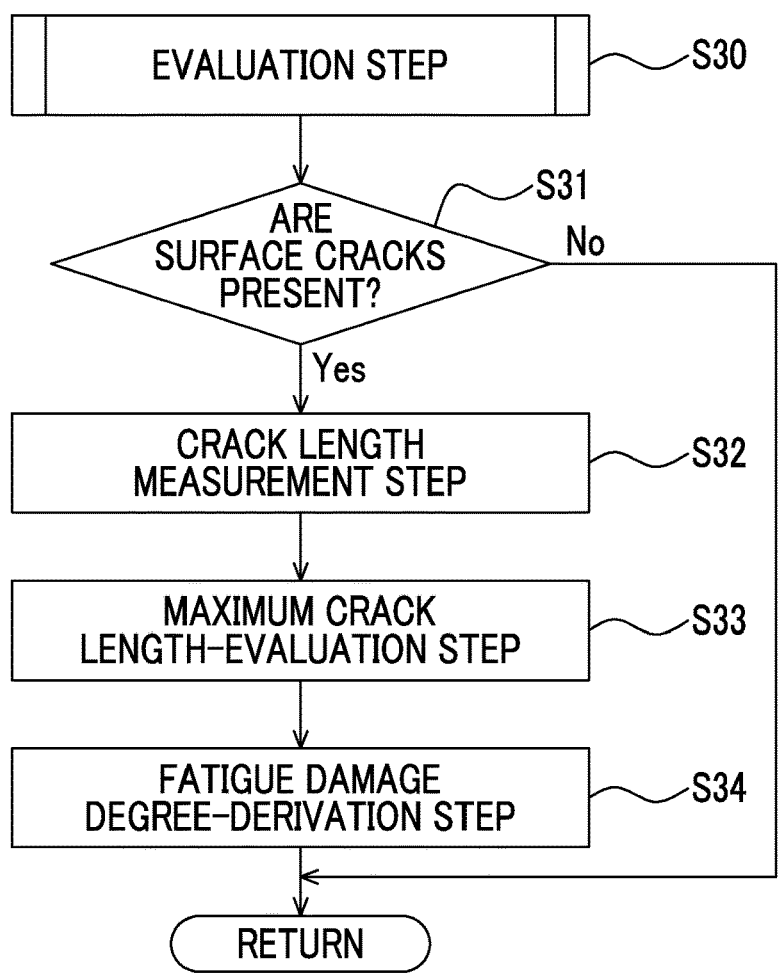
FIG. 14 is a flowchart showing the detailed flow of an evaluation step of the method for evaluating a crack in a metal according to this embodiment.

FIG. 14 is a flowchart showing the detailed flow of the evaluation step of the method for evaluating a crack in a metal according to this embodiment.

After the second removal step S20, the state of the surface cracks 101 of the surface of the metal 100 is evaluated in the evaluation step S30. As shown in FIG. 14, the evaluation step S30 includes a crack presence/absence determination step S31, a crack length measurement step S32, a maximum crack length-evaluation step S33, and a fatigue damage degree-derivation step S34.

It is determined in the crack presence/absence determination step S31 whether or not the surface cracks 101 are present on the surface of the metal 100. Since the oxide scale layer 200 is removed from the metal 100 in the second removal step S20, the surface cracks 101 are exposed in a case where the surface cracks 101 are present on the surface of the base material 102. A method that includes using replica film (acetyl cellulose film) and magnifying and observing the transferred surface of the base material 102 of the metal 100 with a microscope or the like can be applied in the crack presence/absence determination step S31. Further, a method such as directly magnifying and observing the surface of the base material 102 of the metal 100 with a microscope or the like can also be applied. As a result of observation of the surface of the metal 100 performed in this way, in a case where the surface cracks 101 are not generated on the surface of the metal 100, a series of crack evaluation ends.

Further, in a case where the surface cracks 101 are present on the observed surface of the metal 100, the process proceeds to the crack length measurement step S32.

In the crack length measurement step S32, the lengths of the surface cracks 101 are measured on an image observed with a microscope or the like.

In the maximum crack length-evaluation step S33, for example, a general extreme value statistical method, such as Gumbel distribution, is applied on the basis of the measured values of the measured lengths of the plurality of surface cracks 101 to evaluate the maximum length of the surface crack 101.

Figure 15:
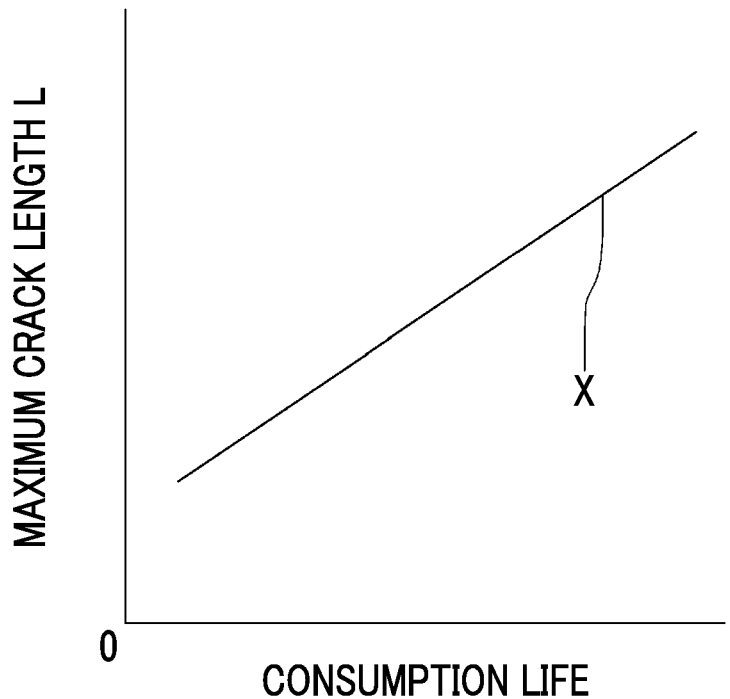
FIG. 15 is a diagram showing an example of master curve information that is used in a fatigue damage degree-derivation step according to this embodiment.

FIG. 15 is a diagram showing an example of master curve information that is used in the fatigue damage degree-derivation step according to this embodiment.

In the fatigue damage degree-derivation step S34, the degree of fatigue damage of the metal 100 is derived on the basis of the evaluation of the maximum length of the surface crack 101 obtained in the maximum crack length-evaluation step S33. The degree of fatigue damage of the metal 100 is derived according to the maximum length of the surface crack 101. For this purpose, for example, master curve information X shown in FIG. 15 is used. The master curve information X shows a correlation between the maximum length of the surface crack 101 and the consumption life of the metal 100. The consumption life of the corresponding metal 100 is specified from the evaluation value of the maximum length of the surface crack 101 obtained in the maximum crack length-evaluation step S33 with reference to the master curve information X, so that the remaining life of the metal 100 is estimated.

The first removal step S10, the second removal step S20, and the evaluation step S30 are sequentially performed in this way, so that the oxide scale layer 200 covering the metal 100 is removed and the surface cracks 101 generated on the surface of the base material 102 of the metal 100 are exposed. Accordingly, the surface cracks 101 can be evaluated.

The master curve information X used in the fatigue damage degree-derivation step S34 can be obtained, for example, as follows.

Figure 16:
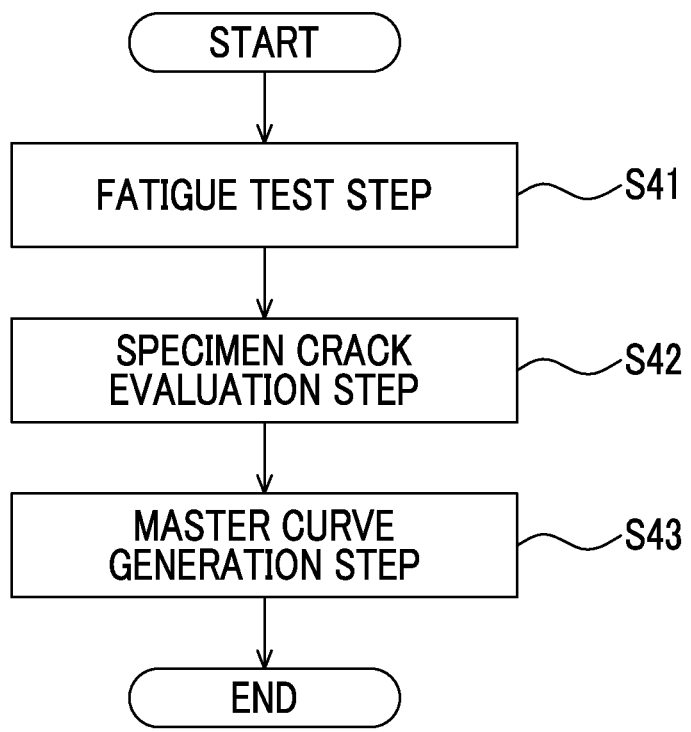
FIG. 16 is a flowchart showing a flow for generating the master curve information according to this embodiment.

FIG. 16 is a flowchart showing a flow for generating the master curve information according to this embodiment.

As shown in FIG. 16, a fatigue test step S41, a specimen crack evaluation step S42, and a master curve generation step S43 are performed to generate the master curve information.

In the fatigue test step S41, a high-temperature low-cycle fatigue test is performed using a plurality of specimens (not shown) made of the same material as the metal 100 that is an object to be evaluated. The fatigue test of the specimen is performed under the same temperature condition as the high-temperature device in which the metal 100 is used, and the number N of repetitions of fracture until the specimen reaches fracture due to the growth of the surface cracks 101 is obtained. A halfway stop test for stopping a test halfway (N/4, N/2, and the like) before reaching the number N of repetitions of fracture is performed on the basis of the number N of repetitions of fracture. Specimens of which the tests are stopped halfway (N/4, N/2, and the like) before reaching the number N of repetitions of fracture are obtained via this halfway stop test. In the plurality of specimens obtained as described above, the surface cracks 101 are generated at ¼ and ½ of a period until a specimen reaches the maximum life up to fracture.

The state of generation of the surface cracks 101 of each specimen obtained in the halfway stop test of the fatigue test step S41 is evaluated in the specimen crack evaluation step S42. An oxide scale layer 200 is generated on the surface of each specimen by the high-temperature low-cycle fatigue test that is performed under the same temperature condition as the high-temperature device in which the metal 100 is used. Accordingly, the oxide scale layer 200 of each specimen is removed, and the surface cracks 101 of the specimen are evaluated in the same process as the method for evaluating a crack in the metal 100 shown in FIG. 2. That is, after the oxide scale layer 200 of each specimen is removed until the scale cracks 201 are exposed in the first removal step S10, the oxide scale layer 200 is completely removed in the second removal step S20, and the state of the surface cracks 101 is evaluated in the evaluation step S30.

The master curve information X showing a correlation between the maximum length of the surface crack 101 and the consumption life of the metal 100 is generated in the master curve generation step S43. For this purpose, the following evaluation equation is obtained from a fatigue life consumption rate ϕF that is determined depending on a period until the test of each specimen is stopped halfway in the fatigue test step S41 and the crack lengths L of the surface cracks 101 that are generated in each specimen.

$$\phi F = f(L)$$

Accordingly, the master curve information X shown in FIG. 15 is obtained.

Therefore, since the oxide scale layer 200 is reliably removed even in a case where the master curve information X used to evaluate damage to the metal 100 is to be obtained, the surface of the material of the specimen can be exposed.

According to the method for evaluating a crack in the metal 100 and the method for evaluating fatigue damage in the metal 100 of the above-mentioned embodiment, scale cracks can be generated on the surface of the oxide scale layer 200 by the first removal step S10. Then, in the second removal step S20, electrolytic treatment is allowed to proceed on the basis of the state of the scale cracks and can be completed at a time when the scale cracks disappear. For this reason, it is possible to suppress that cracks generated on the surface of the base material 102 of the metal 100 cannot be measured correctly since the oxide scale layer 200 remains, or corrosion occurs on the surface of the base material 102 since the electrolytic treatment continues to be performed even after the oxide scale layer 200 has been removed. Accordingly, it is possible to correctly evaluate the cracks of the metal 100 without requiring proficiency.

Further, in the embodiment, electrolytic treatment is performed on the oxide scale layer 200 generated on the surface of the metal 100, the scale cracks 201 generated in the oxide scale layer 200 are confirmed, and electrolytic treatment is then performed repeatedly until the exposed scale cracks 201 disappear. Accordingly, it is possible to suppress that the scale cracks 201 generated in the oxide scale layer 200 are mistaken for the surface cracks 101 generated in the metal 100 and electrolytic treatment ends in a state where the oxide scale layer 200 is not completely removed. Therefore, since the oxide scale layer 200 is reliably removed, the surface of the base material 102 of the metal 100 can be exposed.

In the first determination step S14 of the embodiment, the first master image C1, which is obtained in a state where the scale cracks 201 are generated on the surface of the oxide scale layer 200, and the first image P1 are compared with each other. Accordingly, it is possible to more easily and accurately ascertain that the scale cracks 201 are exposed to the surface of the oxide scale layer 200.

In the second determination step S24 of the embodiment, the second master image C2, which is obtained in a state where the scale cracks 201 have disappeared, and the second image P2 are compared with each other. Accordingly, it is possible to more easily and accurately ascertain that the scale cracks 201 have disappeared.

Further, in the embodiment, an electrolytic treatment time T for which electrolytic treatment is to be performed on the metal 100 in which the scale cracks 201 are generated is set in the second removal step S20 in a case where it is determined that the scale cracks 201 have not disappeared. For this reason, it is possible to suppress that the surface cracks 101 of the metal 100 disappear due to excessive electrolytic treatment.

Furthermore, in the embodiment, the state of scale cracks 201 and the reference image M, which is associated with an electrolytic treatment time T required for the scale cracks 201 to disappear, are compared with each other to set an electrolytic treatment time T for which electrolytic treatment is to be performed on the metal 100 of which the scale cracks 201 are exposed. For this reason, it is easy to appropriately set the electrolytic treatment time T for which electrolytic treatment is to be performed.

Moreover, in the embodiment, an electrolytic treatment time T for which electrolytic treatment is to be performed on the metal 100 in which scale cracks 201 are generated is set on the basis of the growth directions of the scale cracks 201 or the width dimensions of the scale cracks 201. For this reason, it is easy to appropriately set the electrolytic treatment time T for which electrolytic treatment is to be performed.

Further, in the embodiment, electrolytic treatment is performed in a strongly acid solution that does not contain a corrosion inhibitor for inhibiting the corrosion of the metal 100. However, as described above, electrolytic treatment ends in a case where the oxide scale layer 200 is removed and the surface of the base material 102 of the metal 100 is exposed. Accordingly, it is possible to inhibit the corrosion of the surface of the base material 102 that is caused by the strongly acid solution.

The present invention is not limited to the above-mentioned embodiments, and also includes various modifications of the above-mentioned embodiment without departing from the scope of the present invention. That is, the specific shape, configuration, and the like described in the embodiment are merely examples, and can be appropriately changed.

INDUSTRIAL APPLICABILITY

According to the method for evaluating a crack in a metal and the method for evaluating fatigue damage in a metal, it is possible to correctly evaluate the crack of a metal without requiring proficiency.

REFERENCE SIGNS LIST

1: electrolytic cell
2: partition wall
3: electrolytic solution
4: electrode
5: power supply
6: controller
7: imaging device
8: storage device
9: image display unit
10: observation apparatus
100: metal
101: surface crack
102: base material
200: oxide scale layer
201: scale crack
C1: first master image
C2: second master image
M, M1, M2, M3: reference image (master data)
P1: first image
P2: second image
X: master curve information

The invention claimed is:

1. A method for evaluating a crack in a metal, the method comprising:
a first removal step of performing electrolytic treatment on a metal having an oxide scale layer formed on a surface thereof until a scale crack is generated in the oxide scale layer;
a second removal step of removing the oxide scale layer by performing the electrolytic treatment until the scale crack generated in the first removal step disappears; and
an evaluation step of measuring and evaluating a crack formed on a surface of a base material of the metal in which the scale crack has disappeared in the second removal step,
wherein the first removal step includes:
a step of performing the electrolytic treatment on the metal having oxide scale generated on the surface thereof;
a step of acquiring a first image by imaging the oxide scale; and
a step of determining whether or not the scale crack has been generated in the oxide scale on the basis of the first image by comparison of images, and
the second removal step includes:
a step of performing the electrolytic treatment on the metal in which the scale crack is generated;
a step of acquiring a second image by imaging the oxide scale; and
a step of determining whether or not the scale crack has disappeared on the basis of the second image by comparison of images.

2. The method for evaluating a crack in a metal according to claim 1,
wherein in the first removal step, a first master image, which is obtained in a state where the scale crack is generated on a surface of the oxide scale, and the first image are compared with each other in a case where it is to be determined whether or not the scale crack has been generated on the surface of the oxide scale.

3. The method for evaluating a crack in a metal according to claim 1,
wherein in the second removal step, a second master image, which is obtained in a state where the scale crack has disappeared, and the second image are compared with each other in a case where it is to be determined whether or not the scale crack has disappeared.

4. The method for evaluating a crack in a metal according to claim 1,
wherein the second removal step further includes a step of setting a time for which the electrolytic treatment is to be performed on the metal in which the scale crack is generated in a case where it is determined that the scale crack has not disappeared.

5. The method for evaluating a crack in a metal according to claim 4,
wherein master data in which a state of the scale crack is associated with an electrolytic treatment time that is required for the scale crack to disappear, which is set according to the state of the scale crack, is prepared in advance, and
in the step of setting a time for which the electrolytic treatment is to be performed, the time for which the electrolytic treatment is to be performed on the metal in which the scale crack is generated is set on the basis of the second image and the master data.

6. The method for evaluating a crack in a metal according to claim 4,
wherein in the step of setting a time for which the electrolytic treatment is to be performed, the time for which the electrolytic treatment is to be performed on the metal in which the scale crack is generated is set on the basis of a growth direction of the scale crack.

7. The method for evaluating a crack in a metal according to claim 4,
wherein in the step of setting a time for which the electrolytic treatment is to be performed, the time for which the electrolytic treatment is to be performed on the metal in which the scale crack is generated is set on the basis of a width dimension of the scale crack.

8. The method for evaluating a crack in a metal according to claim 1,
wherein the electrolytic treatment is performed in a strongly acid solution that does not contain a corrosion inhibitor for inhibiting corrosion of the metal.

9. A method for evaluating fatigue damage in a metal, the method comprising:
evaluating a degree of fatigue damage of the metal on a basis of a state of a crack formed on the surface of the base material of the metal that is evaluated by the method for evaluating a crack in a metal according to claim 1.

\* \* \* \* \*